United States Patent
Engelman et al.

[11] Patent Number: 5,874,068
[45] Date of Patent: Feb. 23, 1999

[54] STABILIZED ANTIPLAQUE AND ANTIGINGIVITIS ORAL COMPOSITIONS CONTAINING $N^\alpha$-ALKYL-L-ARGININE ALKYL ESTER SALTS

[75] Inventors: E. Eric Engelman, Glen Gardner; Lynn Schick, Columbia; Mona Nair, Morris Plains; R. Michael Buch, Randolph, all of N.J.

[73] Assignee: Warner-Lambert Company, Morris Plains, N.J.

[21] Appl. No.: 986,519

[22] Filed: Dec. 8, 1997

[51] Int. Cl.$^6$ .................. A61K 7/16; A61K 7/22
[52] U.S. Cl. ................... 424/54; 424/49
[58] Field of Search .................. 424/49–58

[56] References Cited

U.S. PATENT DOCUMENTS

| | | | |
|---|---|---|---|
| 4,150,151 | 4/1979 | Pader et al. | 424/56 |
| 4,550,018 | 10/1985 | Ambike et al. | 424/52 |
| 4,657,758 | 4/1987 | Goldemberg et al. | 424/49 |
| 4,666,708 | 5/1987 | Goldemberg et al. | 424/49 |
| 4,945,087 | 7/1990 | Talwar et al. | 424/49 |
| 5,229,103 | 7/1993 | Eagle et al. | 424/49 |
| 5,266,396 | 11/1993 | Ohtsuki et al. | |
| 5,298,238 | 3/1994 | Hussein et al. | 424/49 |
| 5,356,615 | 10/1994 | Gaffar | 424/49 |
| 5,405,604 | 4/1995 | Hall | 424/54 |
| 5,472,685 | 12/1995 | Gaffar | 424/49 |
| 5,681,548 | 10/1997 | Esposito et al. | 424/49 |
| 5,723,106 | 3/1998 | Buch et al. | 424/49 |

FOREIGN PATENT DOCUMENTS

| | | |
|---|---|---|
| 4005221 | 1/1992 | Japan. |
| 9286712 | 11/1997 | Japan. |
| 1352420 | 5/1974 | United Kingdom. |
| WO9311738 | 6/1993 | WIPO. |

*Primary Examiner*—Shep K. Rose
*Attorney, Agent, or Firm*—Evan J. Federman

[57] ABSTRACT

An antiplaque and antigingivitis effective oral composition containing a stabilized $N^\alpha$-acyl acidic amino acid ester salt is disclosed. Also disclosed is a method for inhibiting plaque buildup in the oral cavity with an oral composition containing the stabilized $N^\alpha$-acyl acidic amino acid ester salt.

14 Claims, No Drawings

STABILIZED ANTIPLAQUE AND ANTIGINGIVITIS ORAL COMPOSITIONS CONTAINING $N^\alpha$-ALKYL-L-ARGININE ALKYL ESTER SALTS

BACKGROUND OF THE INVENTION

1. Field of the Invention

This invention relates to antiplaque and antigingivitis effective oral compositions containing stabilized $N^\alpha$-alkyl-L-arginine alkyl ester salts. The invention is also directed to a method for inhibiting plaque in the oral cavity.

2. Description of Related Art

It is known that dental plaque results from the adsorption and propagation of specific oral bacteria on the surface of the teeth. It is also known that the build up of dental plaque on the tooth surface is implicated in the formation of dental caries, as well as gingivitis and alveolar pyorrhea. Therefore, good oral health is critically dependent on the prevention or removal of dental plaque. Brushing the teeth is the most common means employed to reduce plaque build up. However, the effectiveness of brushing has limitations.

Various oral compositions have been formulated in an attempt to control plaque. For example, U.S. Pat. No. 5,266,306 describes an oral composition containing cetylpyridinium chloride as an antibacterial in combination with an $N^\alpha$-cocoyl acyl basic amino acid lower alkyl ester or salt thereof that is said to promote adsorption of cetylpyridinium chloride. Exemplary adsorption promoters include $N^\alpha$-cocoyl-L-arginine methyl ester hydrochloride, $N^\alpha$-cocoyl-L-arginine methyl ester pyrrolidone carboxylate and $N^\alpha$-cocoyl-L-arginine ethyl ester pyrrolidone carboxylate.

GB 1352420 describes lower alkyl esters of mono-N-higher aliphatic acyl arginine having the formula

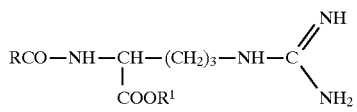

wherein RCO is a higher aliphatic acyl radical containing at least 6 carbon atoms and $R^1$ is a lower alkyl radical containing up to 4 carbon atoms, or salts of the esters, that have antimicrobial or germicidal activity. In particular it is disclosed that $N^\alpha$-cocoyl-L-arginine ethyl ester pyrrolidone carboxylate and $N^\alpha$-cocoyl-L-arginine methyl ester pyrrolidone carboxylate provide bactericidal activity against Escherichia, *Pseudomonas aeruginosa, Proteus vulgarus, Staphylococcus aureus, Bacillus substilis, Candida albicans* and *Aspergillus niger.* It is further asserted that the arginine derivatives provided disinfectant activity against bacterium belonging to the genus Lactobacillus and Staphylococcus. However, this reference neither exemplifies a mouthwash composition nor suggests that the arginine derivatives would be effective against the specific bacterium associated with the formation of plaque.

Arginine esters have been employed in mouthwash compositions as surfactants. JP 04-005221 is directed to mouthwash compositions containing nonwater-soluble components, hydrophilic surfactants, ethanol and water. In particular, this publication describes a mouthwash composition containing vitamin E, N-cocoyl-L-arginine ethyl ester DL-pyrrolidone carboxylate, saccharin, flavor, ethanol and water that is diluted with additional water to give a homogeneous emulsion with an average particle size of 0.44 mm. Such an emulsion would be cloudy. However, mouthwash compositions that are cloudy are disadvantageous since consumers generally require clear single phase mouthwash compositions.

International Publication No. WO 93/11738 describes a dentifrice composition containing a bacteriocin (i.e. an antibacterial agent) such as nisin in combination with a cationic, amphoteric or nonionic surfactant. The D,L-2-pyrrolidone-5-carboxylic acid salt of ethyl-N-cocoyl L arginate is disclosed as a suitable surfactant. JP 57-165305 describes a method for improving the bacteriocidal effect of surfactant type disinfectants such as chlorohexidine digluconate by the addition of $N^\alpha$-cocoyl-L-arginine ethyl ester DL-pyrrolidine carboxylate. The arginine ester is said to have weak bacteriocidal activity, but brings about a synergistic improvement in the bacteriocidal effect of the surfactant type disinfectants.

Ethyl $N^\alpha$-cocoyl-L-arginate pyrrolidone-5-carboxylic acid salt, sold under the tradename CAE®, ethyl $N^\alpha$-lauryl-L-arginate pyrrolidone-5-carboxylic acid salt (hereinafter "LAE") and iso-propyl $N^\alpha$-lauryl-L-arginate pyrrolidone-5-carboxylic acid salt (hereinafter "LAIP") are available from Ajinomoto Co., Inc., Tokyo, Japan. They are said to be useful as disinfectants or bactericidally active ingredients. There is, however, no suggestion or disclosure in the prior art that $N^\alpha$-acyl amino acid ester salts would be effective against the specific microorganisms associated with plaque buildup.

However, aqueous compositions containing salts of $N^\alpha$-alkyl-L-arginine alkyl esters generally undergo hydrolysis reactions typical of esters. Thus, an antiplaque and antigingivitis effective oral composition that contained a stabilized $N^\alpha$-acyl amino acid ester salt would be highly desirable.

SUMMARY OF THE INVENTION

This invention is directed to stabilized antiplaque and antigingivitis oral compositions comprising:

(a) an $N^\alpha$-acyl amino acid ester salt or mixture thereof in an amount of about 0.1 to about 3% by weight of the composition, said $N^\alpha$-acyl acidic amino acid ester represented by the formula

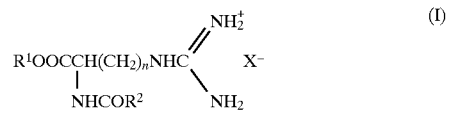

wherein $R^1$ is an alkyl group having 1 to 8 carbons, $R^2$ is an alkyl group having 6 to 30 carbons, n is 1 to 6 and $X^-$ is an anion;

(b) a buffer in an amount effective to provide the composition with a pH below 7;

(c) an alcohol represented by $R^1OH$ in an amount sufficient to stabilize (a); and (d) an aqueous vehicle.

The invention is also directed to a method of inhibiting plaque in an oral cavity comprising the step of introducing stabilized $N^\alpha$-acyl acidic amino acid ester salt into the oral cavity in an amount effective and for a time sufficient to kill microorganisms associated with plaque buildup.

DETAILED DESCRIPTION OF THE INVENTION

The oral compositions of this invention are effective for inhibiting plaque buildup on the surface of teeth and for preventing gingivitis. The $N^\alpha$-acyl acidic amino acid ester salts employed in this invention are described by formula I.

Preferably n is 3 and $R^2$ is an alkyl group having 8 to 18 carbons, with 12 carbons being the most preferred. It is also preferable that $R^1$ has 2 to 4 carbons.

The anion $X^-$ is chloride or DL-pyrrolidone carboxylate and most preferably DL-pyrrolidone carboxylate. The most preferred $N^\alpha$-acyl acidic amino acid ester salts employed in this invention are the DL-pyrrolidone carboxylic acid salts of $N^\alpha$-cocoyl-L-arginine ethyl ester, $N^\alpha$-lauryl-L-arginine ethyl ester and $N^\alpha$-lauryl-L-arginine iso-propyl ester.

The $N^\alpha$-acyl acidic amino acid ester salt is present in the composition in an amount that is effective to inhibit plaque buildup in the oral cavity and that is stable in the oral composition. By stable it is meant that:

1) Solutions remain clear and colorless (NTU's of <20),
2) The pH remains within 0.3 pH units of target,
3) R-factors after accelerated stability testing (3 months at 40° C.) remain <1.00,
4) The concentration of the $N^\alpha$-lauryl-L-arginine alkyl ester salts remains ±10.0% w/v of target after accelerated stability and three years at ambient temperature, and
5) Alcohol concentrations are ±10.0% of target.

The definition of R-factor and NTU will be described below. Unstable $N^\alpha$-acyl acidic amino acid ester salts reduce the antiplaque and antigingivitis efficacy of the composition. Generally, the composition contains the $N^\alpha$-acyl acidic amino acid ester salt in an amount of 0.1 to 3% by weight of the composition. More preferably, the $N^\alpha$-acyl acidic amino acid ester salt is present in an amount between 0.2 to 3% by weight of the composition and most preferably 0.2 to 1.2% by weight of the composition.

The composition also includes an acidic buffer in an amount effective to provide the composition with a pH below 7 and more preferably between about 3 to about 7, most preferably between about 4 to about 5. Generally the amount of acidic buffer is between about 0.05 to about 5% by weight of the composition and more preferably between about 0.1 to about 1% by weight of the composition. Acidic buffers include, but are not limited to, benzoate/benzoic acid, succinate/succinic acid, acetate/acetic acid, and other orally acceptable buffers with dissociation constants within the desired pH range for stability (i.e., pH 3–7, preferably pH 4–5).

The composition includes an alcohol represented by the formula $R^1OH$. The alcohol is present in an amount that inhibits the hydrolysis of the ester of the $N^\alpha$-acyl acidic amino acid ester salt, thereby stabilizing the compound. Preferably the alcohol is present in the composition in an amount of at least 0.01% v/v of the total composition, preferably about 0.05 to about 35% v/v of the total composition and most preferably about 1.0% to about 25% v/v of the total composition.

The aqueous vehicle is generally water, although water/alcohol mixtures may also be employed. The composition may also include flavors; non-ionic, cationic, anionic, or amphoteric surfactants; fluorides; coloring agents; and the like. The additional components are generally known to one skilled in the art.

Exemplary non-ionic surfactants are selected from the group known as poly(oxyethylene)-poly(oxypropylene) block copolymers. Such copolymers are known commercially as poloxamers and are produced in a wide range of structures and molecular weights with varying contents of ethylene oxide. These non-ionic poloxamers are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and about 30 and preferably between about 10 and about 25.

By way of example, non-ionic surfactants useful in this invention include the following poloxamers:

| 105 | 188 | 237 | 334 |
|-----|-----|-----|-----|
| 108 | 215 | 238 | 335 |
| 124 | 217 | 284 | 338 |
| 184 | 234 | 288 | 407 |
| 185 | 235 | 333 |     |

If used, these polymers are present in amounts of from about 0.01% w/v to about 8.0% w/v, and preferably from about 0.10% to about 0.75% w/v. A particularly preferred poloxamer is poloxamer 407 incorporated in an amount of about 0.1 to about 4.5% w/v.

The particular flavor oils and other taste-improving ingredients employed will vary depending upon the particular taste and feel desired. For example, peppermint oil, spearmint oil, or wintergreen flavor may be used. Other flavors such as citrus oils, vanillin and the like may be incorporated to provide further taste variations. Those skilled in the art can select and customize these types of ingredients to provide the desired results. Other conventional ingredients may be used in the oral compositions of this invention, including those known and used in the art. For example, humectants such as polyethylene glycol may be added as an additional solubilizer for the flavor oils and to also provide texture to the composition. These are incorporated in amounts of from about 0.3% w/v to about 1.0% w/v, and preferably about 0.5% w/v. Humectants such as glycerin may be added to enhance the lubricious mouthfeel of the mouthwash and to provide a refreshing, moist, organoleptic feeling thereafter. Glycerin may be incorporated in amounts of from about 1.0% w/v to about 16.0% w/v, and preferably in an amount of about 7.5% w/v. Sweeteners such as aspartame, sodium saccharin, acesulfame K and the like may be added for better taste in amounts of from about 0.005% w/v to about 1.0% w/v. Sorbitol may also be included in the composition of this invention in an amount up to about 25%.

Zinc chloride may be added as an astringent for an "antiseptic cleaning" feeling in an amount of from about 0.0025% w/v to about 0.75% w/v. Although the mouthwash formulations of the present invention may be formulated to be substantially clear and colorless, approved food dyes are preferably used to provide a pleasing color to the formulations of the invention. These may be selected from the long list of acceptable food dyes. Suitable agents for this purpose include FD&C yellow #5, FD&C yellow #10 and FD&C green #3.

Water is added to q.s. the composition and the composition may then be bottled and packaged for shipping.

This invention will be better understood from the experimental details that follow. However, one skilled in the art will readily appreciate that the specific method and results discussed are merely illustrative of the invention and no limitation of the invention is implied.

EXPERIMENTAL DETAILS

R-Factor

A convenient measure of the antimicrobial efficacy of the compositions of the present invention is known as the "R-factor." The R-Factor is defined as: the ratio of (a) the time required for a oral composition to completely kill Streptococcus mutans in biofilms grown in vitro on stainless steel wires, to (b) the time required for a standard Listerine® mouthwash composition to completely kill S. mutans in biofilms grown in vitro on identical stainless steel wires. The time required to completely kill S. mutans in biofilms is defined as the "critical kill time" or "CKT." This time is measured in minutes. The stabilized oral compositions of the present invention exhibit an R-factor of less than about 1.0, and most often less than about 0.8.

Plaque Penetration

Critical kill time is determined using a plaque penetration assay. The plaque penetration assay used by the present inventors is a modification of the well-known procedure of Tanzer, et al., described or referenced in, e.g., Tanzer, et al., "Structural requirements of Guanide, Biguanide and Bis-biguanide Agents for Antiplaque Activity," *Antimicrobial Agents and Chemotherapy*, December 1977, pp. 721–729; and Tanzer, et al., "In Vitro Evaluation of Seven Cationic Detergents as Antiplaque Agents," *Antimicrobial Agents and Chemotherapy*, March 1979, pp. 408–414.

The mouthwash composition used as the standard for the plaque penetration assay contains 27% v/v ethanol. A one liter batch is prepared having the composition shown in Table 1.

TABLE 1

| Ingredient | Amount |
| --- | --- |
| Ethanol (USP) | 284 mls |
| Thymol | 0.64 gram |
| Eucalyptol | 0.92 gram |
| Menthol | 0.42 gram |
| Methyl Salicylate | 0.64 gram |
| Benzoic Acid | 1.5 grams |
| Caramel | 0.2 gram |
| Poloxamer 407 | 1.0 gram |
| Water | Q.S. to 1 Liter |

The media required for the plaque penetration assay include sterile deionized water; Letheen Broth (DIFCO); and Jordan's complex medium (with and without bromocresol pure pH indicator) [see Jordan, H. V. et al. *J. Dent. Res.* 39: 116–123 (1960)]. The equipment requirements for the assay include a large number of sterile glass test tubes (e.g., 13×100 millimeters); test tube racks to hold multiple rows of sample tubes; an autoclave; and stainless steel Nichrome wires (1.5×85 mm). It is convenient to attach each plaque wire to a Morton Closure by any suitable means, such as welding.

Jordan's complex medium may be prepared by blending the following ingredients with heating as necessary:

| Ingredient | Amount |
| --- | --- |
| Trypticase Peptone (BBL) | 5 grams |
| Yeast Extract | 5 grams |
| $K_2HPO_4$ | 5 grams |
| Stock Salts Solution (see below) | 0.5 ml |
| Sucrose | 50 grams |
| Sodium Carbonate | 0.05 grams |
| Deionized Water | Q.S to 1 Liter |

Stock Salts Solution

| Ingredient | Concentration |
| --- | --- |
| $MgSO_4$ (anhydrous) | 3.9 g/L |
| $FeCl_3 \cdot 6H_2O$ | 0.4 g/L |
| $MnCl_2$ (anhydrous) | 0.12 g/L |
| Distilled water | Q.S. to 1 Liter |

The pH is adjusted to 7.1 with 5N HCl followed by cooling to room temperature, if necessary. 50 ml is removed from the batch and placed in a 100 milliliter flask. Jordan's medium with pH indicator ("recovery medium") is prepared by adding 1 ml of a 1% bromocresol purple stock solution (i.e., 0.1 gram bromocresol purple in 10 mls distilled water) to 1 liter of Jordan's medium.

The culture for the assay is prepared as follows: Upon receipt, the ATCC culture is rehydrated and subcultured according to the directions supplied by the American Type Culture Collection. The subculture is streaked for purity on Brain-Heart Infusion Agar (DIFCO) and inoculated into 100 ml of sterile BHI. The agar plates are examined for purity after 14–18 hours. If acceptable, 11 ml of sterile glycerin are added to the BHI culture, vortexed and then subdivided into 1.8 ml cryogenic tubes. The cultures are then stored at –80° C.

Four days prior to an assay, a frozen vial is thawed and added to the small, 100 ml flask containing 50 ml of Jordan's medium to start the cultures used for the biofilm assay. After 14–18 hours, the contents of the small flask are decanted aseptically into 2 liters of Jordan's medium. The resulting inoculated medium is then aseptically dispensed, in 5.0 ml portions, into a number of empty sterile test tubes, each tube having a plaque wire-equipped Morton cap. The inoculated tubes are then incubated anaerobically overnight (i.e., 14–16 hours) at 37° C.

The number of test tubes will vary depending upon the number of different mouthwash samples being tested, but it will be convenient to describe an assay of a standard high ethanol mouthwash and four reduced ethanol mouthwash samples, which requires racks each holding 75 test tubes (i.e., five rows of fifteen tubes, each row comprising five sets of three tubes each). The first set of three tubes in each row is usually reserved for the standard high ethanol mouthwash, with the succeeding four sets of three tubes each in that row being reserved for the four reduced ethanol samples. There are three tubes in each set because each assay is performed in triplicate.

After the overnight incubation, the plaque wires are then transferred into fresh Jordan's medium in 75 tubes (in a second rack) and again incubated anaerobically for 24 hours at 37° C. This procedure is repeated once more. Thus, the plaque wires are cultured for 3 days, with two transfers after initial inoculation.

On the third day, just prior to the assay, five additional racks (each containing 75 sterile test tubes) are prepared: a first (assay) rack whose test tubes each contain 6 ml of the sample mouthwashes; a second (water) rack whose test tubes each contain 6 ml of sterile deionized water; third and fourth racks whose test tubes each contain 6 ml of Letheen broth rinse; and a fifth rack whose test tubes each contain 5 ml of Jordan's recovery medium. For convenience, the racks may be marked for test series identity and time (by row).

Assay Procedure

Each assay involves triplicate testing at time points separated by one minute intervals, e.g., at 2, 3, 4, 5 and 6 minutes of mouthwash treatment. The first (or bottom) row of each rack corresponds to the first test time and the succeeding four rows correspond, respectively, to the next four test times. The exact time of exposure of the plaque wires to the sample mouthwashes can be varied according to the thickness of the "plaques". Ideally, the exposure period will result in positive microorganism growth in the first one or two sampling intervals of the high ethanol control group, (i.e., the first and second row) and no growth thereafter. Establishing lower and upper limits of exposure required for complete kill by the control mouthwash permits an accurate comparison of the four sample mouthwashes to this control. Mouthwash exposure takes place in a 37° C. New Brunswick shaking water bath (shake speed 3) and may be staggered so that the 5 time points are run concurrently, but with sufficient time to permit accurate timing and handling.

(1) To start the assay, transfer one row of plaque wires to the first (bottom) row of tubes in the rack containing 6 ml of sterile water. Leave in place 2 minutes. Repeat for the next four rows of plaque wires.

(2) After the water rinse, transfer each row of plaque wires into the appropriate, corresponding, row of tubes in the rack containing 6 ml of test mouthwash. Leave each row of plaque wires in place, with shaking in the 37° C. water bath, for its treatment (exposure) period; i.e., remove the rows of plaque wires sequentially at 5 preset time points so that each succeeding row of plaque wires is exposed to a mouthwash for successively longer periods of time (e.g., 2, 3, 4, 5 and 6 minutes; individual timing can vary according to estimated "plaque" thickness.

(3) For each row of plaque wires, at the end of its treatment period, immediately remove the row and place it in the appropriate corresponding row of the first rack of 6 ml Letheen Broth neutralization/rinse tubes. Leave each row of wires in that broth for 5 minutes and then transfer it to the appropriate corresponding row of the second rack of 6 ml Letheen Broth rinse tubes.

(4) At the end of the second Letheen Broth rinse, remove each row of plaque wires and place it in the appropriate corresponding row of the rack of 6 ml Jordan's recovery medium (with bromocresol purple). Incubate anaerobically for 48 hours at 37° C.

(5) Read for growth (+) or no growth (−) at 48 hours. Positive growth is indicated by a color change from purple to yellow (i.e., if the microorganism is still viable, it will produce an acid that causes the color change); positive growth is often accompanied by an increase in broth turbidity.

Determination of Critical Kill Times and R-Factor

Since each mouthwash sample is located in the same set of three tubes in each row of the rack, the critical time necessary for the sample to completely kill the S. mutans can be determined by observing the point (front to back or bottom to top, as the case may be) at which the Jordan recovery medium color changed from yellow to purple. The CKT for any sample divided by the CKT for the control mouthwash in that same rack is the R-Factor for that sample.

Table 2 below summarizes a statistical scale that relates the observed change from growth (+) to no growth (−) to critical kill times. For example, as shown in the first row of Table 2, where the observed condition changes from growth (continuous +'s) to no growth (continuous −'s) ("no anomaly"), the critical kill time is determined by adding 0.50 minute to the time at which the last growth observation (+) was made. The balance of Table 2 sets forth how critical kill times are determined for different observed growth/no growth intervals between continuous growth segments and continuous no growth segments.

TABLE 2

| BUSCH Scores For Critical Kill Times (CKT) | |
|---|---|
| Intervals between continuous +'s and −'s | Add To Last (+) Time |
| No anomaly | 0.50 |
| −+ | 1.50 |
| −++ | 2.90 |
| −+++ | 4.10 |
| −+−+ | 2.50 |
| −+−−+ | 2.10 |
| −++−+ | 4.06 |
| −−+ | 1.10 |
| −−++ | 2.50 |
| −−+−+ | 3.84 |
| −−−+ | 0.90 |
| −−−−+ | 0.80 |

By way of further example, consider the examples of growth/no growth sequences, and their associated critical kill times, in Table 3. In the first row of Table 3, there was no anomaly between continuous +'s and continuous −'s; therefore, CKT (per Table 2)=4.0+0.5=4.5 minutes (i.e., kill occurred somewhere between 4.0 and 5.0 minutes). In the second row of Table 3, the interval between continuous +'s and continuous −'s is −+; therefore, CKT (per Table 2)=2.0+1.5=3.5 minutes.

TABLE 3

| Examples of Growth/No Growth Sequences and CKT | | | | | |
|---|---|---|---|---|---|
| Treatment Times (min) | | | | | |
| 2.0 | 3.0 | 4.0 | 5.0 | 6.0 | CKT |
| + | + | + | − | − | 4.5 |
| + | − | + | − | − | 3.5 |
| + | + | + | + | + | >6.5 |
| − | − | − | − | − | <2.0 |
| + | − | − | + | − | 3.1 |

In the case of rows 3 and 4 of Table 3, clearly no end point was reached. It is assumed here that kill will occur at some point in excess of 6.5 minutes (>6.5) or much below 2.0 minutes (<2.0), respectively.

Row 5 (Table 3) is an example where the kill scale is dependent on the values that are located to the left of the last + and to the right of the first −. For that particular example, CKT=2.0+1.1=3.1 minutes (per Table 2).

EXAMPLES

The stabilizing effects of pH, various buffering agents, buffering capacity and alcohol concentration were determined by preparing several aqueous/hydroalcoholic compositions of D,L-pyrrolidone carboxylic acid salts of $N^\alpha$-lauryl-L-arginine ethyl ester (LAE) containing assorted mixtures of the above categories of compounds.

Comparative Examples 1–3

An initial study was performed to determine the effect of the amount of ethanol. Each example contained ethanol, LAE, 0.15% w/v benzoic acid (BA, pH adjusted to 4.2) and water to q.s. The ingredients are mixed in a beaker and placed in a sealed glass container, which is then put in a 40°

C. oven for three months. After three months the samples are measured for the amount of ethanol, pH, amount of LAE and NTU. The NTU (nephelometric turbidity unit) is measured by a ratio turbidimeter that uses a beam of light directed through the test sample. Detectors are placed to measure the 90 degree light scatter, the forward light scatter and the light transmitted through the sample. The comparative examples and the results of the stability study are summarized in Table 4.

TABLE 4

|  |  |  | Initial |  |  | 3 Month/40° C. |  |  |  |
|---|---|---|---|---|---|---|---|---|---|
| Comp. Ex. No. | % v/v EtOH | LAE % w/v | pH | R-Factor | NTU | LAE % w/v | pH | R-Factor | NTU |
| 1 | 0.0 | 0.459 | 4.23 | <0.63 | 23 | 0.308 (67.1%) | 3.98 | — | >200 |
| 2 | 2.0 | 0.448 | 4.25 | <0.65 | 13 | 0.311 (69.4%) | 4.01 | — | >200 |
| 3 | 10.0 | 0.471 | 4.24 | <0.69 | 10 | 0.357 (75.8%) | 3.96 | — | 110 |

Ethanol concentrations (% v/v) remained stable throughout the investigation. The percent LAE remaining after the accelerated stability is shown in parentheses in Table 4. In-vitro antimicrobial experiments (determination of the R-factor) were not performed on the accelerated stability prototypes due to the extreme turbidity of the mouthrinses. However, in-vitro kinetic biofilm assays were performed on the 2 and 10% v/v ethanol 3M/30° C. samples (0.380 and 0.402% w/v LAE remaining). The R-Factors for both of these 30° C. stability samples were <0.60.

Comparative examples 1–3 indicate that the amount of ethanol effects the stability of LAE. However, in order to obtain a stable LAE containing mouthwash composition using only the ethanol level as the stabilizing component would produce a mouthwash with an unacceptably high level of ethanol.

A second LAE mouthrinse stability study was initiated to evaluate the stabilizing effects of increasing ethanol concentrations to 35% v/v, the use of succinic acid and increases in buffering capacity of both SA and BA. The examples are made in the same manner as Comparative Examples 1–3. The results of the second stability investigation are described below in Table 5.

No R-factor was determined for Comparative Example 4 because of the extreme turbidity of the example. The results of the second stability investigation clearly indicate the significance of ethanol concentration, buffering capacity and usage of a proper buffering system in the stabilization of LAE in hydroalcoholic mouthwash formulations.

Other variations and modifications of this invention will be obvious to those skilled in this act. This invention is not limited except as set forth in the following claims.

What is claimed is:

1. An oral composition comprising:
   (a) an $N^{\alpha}$-acyl acidic amino acid ester salt or mixture thereof in an amount of about 0.1 to about 3% by weight of the composition, said $N^{\alpha}$-acyl acidic amino acid ester represented by the formula $$R^1OOCCH(CH_2)_n NHC\overset{\displaystyle NH_2^+}{\underset{\displaystyle NH_2}{\diagup}} \quad X^- \qquad (I)$$
$$\underset{\displaystyle NHCOR^2}{|}$$

wherein $R^1$ is alkyl having 1 to 8 carbons, $R^2$ is alkyl having 6 to 30 carbons, n is 1 to 6 and $X^-$ is an anion;
   (b) an acidic buffer in an amount effective to provide said composition with a pH from about 3 to below 7;
   (c) an alcohol represented by $R^1OH$ in an amount of at least 0.05% v/v to about 35% v/v of the total composition in an amount sufficient to actively inhibit the hydrolysis of the ester of (a); and
   (d) an aqueous mouthwash vehicle.

2. The oral composition according to claim 1, wherein n is 3 and $R^2$ is an alkyl group having 12 to 18 carbons.

TABLE 5

|  |  |  | Initial |  |  | 3 Month/40° C. |  |  |  |
|---|---|---|---|---|---|---|---|---|---|
| EX NO. | EtOH % v/v | Buffer (% w/v) | LAE % w/v | pH | NTU | LAE % w/v | pH | R-Factor | NTU |
| Comp Ex.4 | 10.0 | BA 0.15 | 0.565 | 4.19 | 16.2 | 0.429 (75.9%) | 3.39 | — | 85 |
| 1 | 10.0 | SA 0.145 | 0.545 | 4.20 | 4.4 | 0.504 (92.5%) | 4.15 | 0.57 | 0.23 |
| 2 | 10.0* | SA 0.58 | 0.515 | 4.21 | 2.7 | 0.487 (94.6%) | 4.21 | 0.7 | 0.31 |
| 3 | 20.0 | BA 0.15 | 0.542 | 4.20 | 11.2 | 0.489 (90.2%) | 4.13 | 0.57 | 0.22 |
| 4 | 20.0 | SA 0.145 | 0.547 | 4.23 | 5.3 | 0.527 (96.3%) | 4.25 | 0.57 | 0.05 |
| 5 | 35.0 | BA 0.60 | 0.544 | 4.17 | 7.7 | 0.537 (98.7%) | 4.16 | 0.57 | 0.11 |

3. The oral composition according to claim 2, wherein $R^1$ is ethyl.

4. The oral composition according to claim 2, wherein $R^1$ is iso-propyl.

5. The oral composition according to claim 1, wherein said acidic buffer is succinic.

6. The oral composition according to claim 1, wherein $X^-$ is selected from the group consisting of DL-pyrrolidone carboxylate or chloride.

7. The oral composition according to claim 1, wherein said $N^\alpha$-acyl acidic amino acid ester is selected from the group consisting of DL-pyrrolidone carboxylic acid salt of $N^\alpha$-lauryl-L-arginine iso-propyl ester and DL-pyrrolidone carboxylic acid salt of $N^\alpha$-lauryl-L-arginine ethyl ester.

8. A method for inhibiting plaque in an oral cavity comprising the step of introducing to the oral cavity an oral composition comprising:

(a) an $N^\alpha$-acyl acidic amino acid ester salt or mixture thereof in an amount of about 0.1 to about 3% by weight of the composition, said $N^\alpha$-acyl acidic amino acid ester represented by the formula

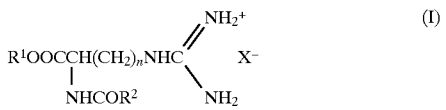 (I)

wherein $R^1$ is alkyl having 1 to 8 carbons, $R^2$ is alkyl having 6 to 30 carbons, n is 1 to 6 and $X^-$ is an anion;

(b) an acidic buffer in an amount effective to provide said composition with a pH from about 3 to below 7;

(c) an alcohol represented by $R^1OH$ in an amount of at least 0.05% v/v to about 35% v/v of the total composition in an amount sufficient to actively inhibit the hydrolysis of the ester of (a); and (d) an aqueous mouthwash vehicle.

9. The method according to claim 4, wherein n is 3 and $R^2$ is an alkyl group having 12 to 18 carbons.

10. The method according to claim 9, wherein $R^1$ is ethyl.

11. The method according to claim 9, wherein $R^1$ is iso-propyl.

12. The method according to claim 8, wherein said acidic buffer is succinic.

13. The method according to claim 8, wherein $X^-$ is selected from the group consisting of DL-pyrrolidone carboxylate or chloride.

14. The method according to claim 8, wherein said $N^\alpha$-acyl acidic amino acid ester is selected from the group consisting of DL-pyrrolidone carboxylic acid salt of $N^\alpha$-lauryl-L-arginine iso-propyl ester and DL-pyrrolidone carboxylic acid salt of $N^\alpha$-lauryl-L-arginine ethyl ester.

* * * * *